(12) United States Patent
Mogensen et al.

(10) Patent No.: US 12,226,304 B2
(45) Date of Patent: Feb. 18, 2025

(54) CLOSURE MECHANISM

(71) Applicant: Cook Medical Technologies LLC, Bloomington, IN (US)

(72) Inventors: John Mogensen, Hvidovre (DK); Nuno Dias, Malmo (SE)

(73) Assignee: Cook Medical Technologies LLC, Bloomington, IN (US)

( * ) Notice: Subject to any disclaimer, the term of this patent is extended or adjusted under 35 U.S.C. 154(b) by 550 days.

(21) Appl. No.: 17/678,673

(22) Filed: Feb. 23, 2022

(65) Prior Publication Data
US 2022/0265416 A1    Aug. 25, 2022

(30) Foreign Application Priority Data

Feb. 24, 2021    (GB) ..................................... 2102612

(51) Int. Cl.
*A61F 2/06*     (2013.01)
*A61L 27/50*    (2006.01)
*A61M 39/04*    (2006.01)

(52) U.S. Cl.
CPC .............. *A61F 2/06* (2013.01); *A61L 27/507* (2013.01); *A61M 39/04* (2013.01)

(58) Field of Classification Search
CPC ...... A61F 2/04; A61F 2/06; A61F 2/07; A61F 2/954; A61F 2/95; A61F 2/848; A61F 2002/9511
See application file for complete search history.

(56) References Cited

U.S. PATENT DOCUMENTS

| | | |
|---|---|---|
| 2012/0123523 A1 | 5/2012 | Hartley et al. |
| 2016/0270794 A1 | 9/2016 | Block |
| 2021/0205066 A1* | 7/2021 | Geusen ...................... A61F 2/07 |
| 2022/0015891 A1* | 1/2022 | Shipley ...................... A61F 2/07 |

FOREIGN PATENT DOCUMENTS

GB    2527550 A    12/2015

OTHER PUBLICATIONS

Great Britain Search Report, dated Jul. 9, 2021, 1 pg., issued in GB Patent Application No. BG2102612.5, Intellectual Property Office, Newport, South Wales, UK.

* cited by examiner

*Primary Examiner* — Diane D Yabut
(74) *Attorney, Agent, or Firm* — Crowell & Moring LLP

(57) ABSTRACT

A closure mechanism for closing a tubular portion of a graft that includes a closure element having aperture or looped ends. The closure element is provided around the circumference of a tubular length of graft material and is attached thereto. The closure element is biased into an annular profile by threading a release element through the ends holding them together. In its annular profile, the closure element thus holds the lumen of the tubular length of graft material in an open configuration. Withdrawal of the release element causes the closure element to take on a flat/linear profile, pulling the lumen closed as it does so. The closure mechanism can be used in a vascular implant such as a graft, stent graft, including tubular, bifurcated, and branched stent grafts, an occlusion device, or the like.

20 Claims, 9 Drawing Sheets

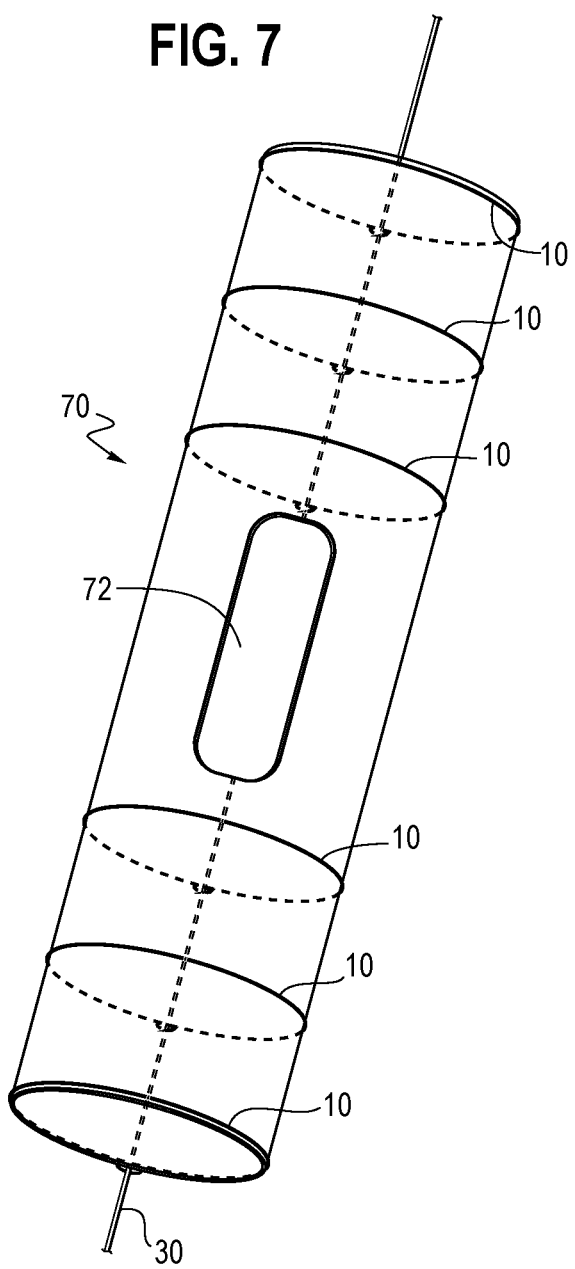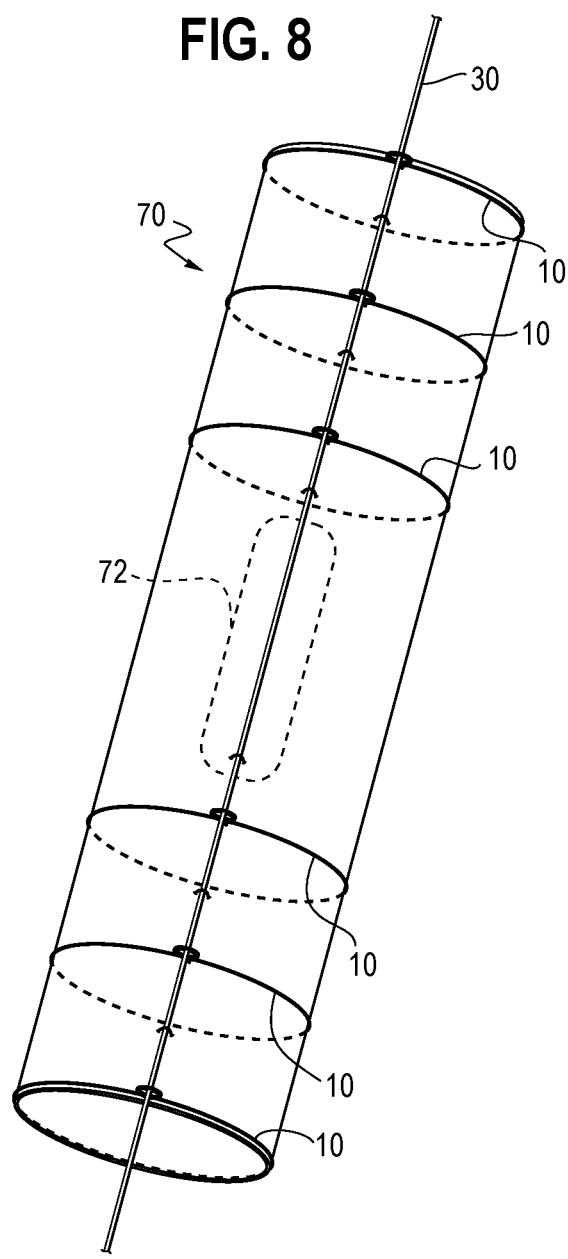

CLOSURE MECHANISM

RELATED APPLICATIONS

This application claims the benefit of priority to Great Britain Patent Application No. 2102612.5, filed Feb. 24, 2021, and entitled "Closure Mechanism," the entire contents of which is incorporated herein by reference.

TECHNICAL FIELD

The present invention relates to a closure mechanism for a vascular implant, and to vascular implants including such a closure mechanism. In particular it relates to an occlusion device such as a candy plug (false lumen occluder), a bidirectional branch graft, and a selectively closable bifurcated endoluminal prosthesis including a closure mechanism.

BACKGROUND

A variety of vascular implants are well known and widely used. For example, stents, with or without associated graft material, may be used at various locations throughout a patient's vasculature to maintain or enhance blood flow where blockage has occurred. Vascular plugs, or occluders, are well known for occluding bodily vessels and are produced in a variety of forms.

Stents and stent grafts are often designed for use in a specific area of a patient's vascular anatomy. This reduces the flexibility of a given device, and the design often means that the surgeon is obliged to use it in a particular way.

Vascular plugs may act to create substantially instantaneous occlusion of a vessel, in which case the structure of the plug provides an impermeable barrier to fluid, or they may act to occlude the vessel over time, in which case the plug will generally have a pervious membrane designed to slow the flow of blood through the vessel. The membrane promotes thrombosis of the blood and eventual occlusion of the vessel by the formed thrombus. This does not happen reliably, and in some instances it can take several months, which can be problematic.

U.S. Pat. No. 9,427,307 relates to circumferentially constraining sutures for a stent-graft.

U.S. Pat. No. 8,808,355 relates to a stent graft having a closable fenestration.

U.S. Pat. No. 9,265,599 relates to a retention system for an endoluminal device.

US 2019/0231571 relates to a delivery system and method to radially constrict a stent graft.

EP 3 470 017 and US 2019/0021887 relate to a method of making an internal bidirectional branch.

EP 3 421 011 relates to an implantable device including a valve member.

The present invention seeks to provide an improved closure mechanism for a vascular implant, an improved graft assembly, an improved bifurcated endoluminal prosthesis, an improved vascular implant, an improved valve element, an improved occlusion device, and an improved introducer assembly for deploying a vascular implant.

SUMMARY OF THE INVENTION

According to an aspect of the present invention, there is provided a closure mechanism for a vascular implant, the vascular implant including a tubular portion providing a lumen having a circumference defined by the tubular portion, the closure mechanism including at least one closure element extending around the circumference of the tubular portion and attached to the tubular portion, the at least one closure element being made of a resiliently deformable material and having a first, biased, configuration in which the closure element has a generally annular profile and a second, unbiased, configuration in which the closure element has a substantially flat profile; wherein in the biased configuration the closure element holds the tubular portion lumen in an open configuration and in the unbiased configuration the closure element closes the tubular portion lumen; the mechanism also including a release element engaged with the closure element, wherein disengaging the release element allows the closure element to convert from its generally annular profile to its substantially flat profile, thereby closing the tubular portion lumen.

According to another aspect of the present invention, there is provided a graft assembly including a tubular main body portion providing a main graft lumen, a tubular branch coupling insert disposed within the main body portion and providing a coupling insert lumen and having at least one coupling insert circumference, the coupling insert including at least one closure element extending around the coupling insert circumference and attached to the branch coupling insert, the at least one closure element being made of a resiliently deformable material and having a first, biased, configuration in which the closure element has a generally annular profile and a second, unbiased, configuration in which the closure element has a substantially flat profile; wherein in the biased configuration the closure element holds the coupling insert lumen in an open configuration and in the unbiased configuration the closure element closes the coupling insert lumen.

The graft assembly may comprise a plurality of closure elements disposed along a length of the coupling insert.

The plurality of closure elements may be disposed in spaced relationship along the coupling insert.

The coupling insert may be a bidirectional member having first and second branch portions, the first and second branch portions being coupled to the main graft and such that the coupling insert lumens of the first and second branch portions are in fluid communication with the main graft lumen, wherein the at least one closure element is disposed on at least one of the branch portions.

Closure elements may be provided on each of the branch portions, thereby being able selectively to close one or both of the branch portions.

The graft assembly may include a release element operable to hold the at least one closure element in the biased configuration.

The graft assembly may include a branch graft configured to be disposed in the branch coupling insert, the branch graft including at least one scaffold for expanding or maintaining the branch graft in an open tubular configuration when disposed in the branch coupling insert.

According to another aspect of the present invention, there is provided a bifurcated endoluminal prosthesis including a main body portion, a first leg portion and a second leg portion, the leg portions extending distally from the main body portion, wherein at least the first leg portion includes at least one closure element extending around a circumference of the first leg portion and attached to the first leg portion, the at least one closure element being made of a resiliently deformable material and having a first, biased, configuration in which the closure element has a generally annular profile and a second, unbiased, configuration in which the closure element has a substantially flat profile;

wherein in the biased configuration the closure element holds the first leg portion in an open configuration and in the unbiased configuration the closure element closes the first leg portion.

The prosthesis may comprise a plurality of closure elements disposed along a length of the first leg portion. The plurality of closure elements may be disposed in spaced relationship along the first leg portion.

The prosthesis may include a release element operable to hold the at least one closure element in the biased configuration.

In any of a closure mechanism, graft assembly or prosthesis the at least one closure element may be a wire of resiliently deformable material.

The closure element may have first and second ends, each end including a fixation point, wherein, when the ends are fixed adjacent or over one another, the closure element is held in the annular configuration and when the ends are released, the closure element adopts the substantially flat profile.

The or each closure element may have in the biased configuration an annular ring shape.

The fixation points may be looped or apertured ends of the closure element.

The at least one closure element may be made of spring metal or a shape memory material.

The at least one closure element may be made of spring steel or nickel titanium alloy.

According to another aspect of the present invention, there is provided a vascular implant having a tubular portion, including a closure mechanism as defined above.

In an embodiment, the closure element is attached around approximately half the circumference of the tubular portion, and preferably around only half the circumference.

According to another aspect of the present invention, there is provided a valve element including a closure mechanism as defined above.

According to another aspect of the present invention, there is provided an occlusion device including a valve element as defined above, wherein the closure mechanism is operable to provide occlusion of a blood vessel upon disengagement of the release element.

The occlusion device may be a candy plug.

According to another aspect of the present invention, there is provided an introducer assembly for deploying a vascular implant as defined above including a closure mechanism as defined above, or for deploying a graft assembly as defined above, or for deploying a prosthesis as defined above, or for deploying an occlusion device as defined above, the introducer assembly including an elongate carrier element configured to carry the vascular implant, graft assembly, prosthesis or occlusion device, wherein at least one release element is connected to the at least one closure element and configured to bias the at least one closure element in the biased configuration on deployment of the graft or implant, the release element maintaining the lumen in an open configuration until removal of the release element.

The introducer assembly may include a second elongate carrier configured to carry a branch graft, the second elongate carrier being configured to deploy the branch graft into at least a portion of the branch coupling insert.

The branch coupling insert may be a bidirectional member having first and second branch portions, the first and second branch portions being coupled to the main graft such that the coupling insert lumens of the first and second branch portions are in fluid communication with the main graft lumen, wherein closure elements are provided on each of the branch portions, the at least one release element being releasably engaged with the closure elements.

According to another aspect of the present invention, there is provided a method of deploying a graft assembly including a tubular main body portion providing a main graft lumen, a tubular branch coupling insert disposed in the main body portion and providing a coupling insert lumen and having at least one coupling insert circumference, the coupling insert including at least one closure element extending around the coupling insert circumference and attached to the branch coupling insert, the at least one closure element being made of a resiliently deformable material and having a first, biased, configuration in which the closure element has a generally annular profile and a second, unbiased, configuration in which the closure element has a substantially flat profile; the method including the steps of: deploying the graft assembly in a vessel of a patient with the closure element in the biased configuration so as to the hold the coupling insert lumen in an open configuration; removing the bias in the closure member to allow the closure member to return to the unbiased configuration thereby to cause the closure element to close the coupling element lumen.

The method may include the step of disposing a branch graft in the branch coupling insert while the coupling insert lumen is in the open configuration.

The branch coupling insert may be a bidirectional member having first and second branch portions, the first and second branch portions being coupled to the main graft such that the coupling insert lumens of the first and second branch portions are in fluid communication with the main graft lumen, wherein closure elements are provided on each of the branch portions; and the method may include the step of: closing the first branch portion so as to close fluid access to the first branch portion, and leaving the second branch portion open.

The method may include the step of disposing a branch graft in the first branch portion and releasing the bias on at least the second branch portion thereby to close the second branch portion.

The method may include the step of disposing a branch graft in the first branch portion and releasing the bias on both the first and second branch portions, whereby a scaffold provided on the branch graft maintains the first branch portion in the open configuration.

According to another aspect of the present invention, there is provided a method of deploying a bifurcated endoluminal prosthesis including a main body portion a first leg portion and a second leg portion, the leg portions extending distally from the main body portion, wherein at least the first leg portion includes at least one closure element extending around a circumference of the first leg portion and attached to the first leg portion, the at least one closure element being made of a resiliently deformable material and having a first, biased, configuration in which the closure element has a generally annular profile and a second, unbiased, configuration in which the closure element has a substantially flat profile; the method including the steps of: deploying the bifurcated endoluminal prosthesis in a vessel of a patient with the closure element in the biased configuration so as to the hold the first leg portion in an open configuration; removing the bias in the closure member to allow the closure member to return to the unbiased configuration thereby to cause the closure element to close the first leg portion.

The method may include the step of disposing a scaffold in the first leg portion while the first leg portion is in the open configuration.

Other aspects, features and advantages of the teachings herein are set out in the specific description that follows.

BRIEF DESCRIPTION OF THE DRAWINGS

Embodiments of the present invention are described below, by way of example only, with reference to the accompanying drawings, in which:

FIG. 7 is a perspective view of an internal bidirectional coupling insert;

FIG. 8 is a perspective view of the insert of FIG. 7 from the opposite side;

DESCRIPTION OF THE PREFERRED EMBODIMENTS

The term "vascular implant" refers to any device for insertion or implantation into or replacement for a body part or a function of that body part within the vascular system of a patient. The term also may refer to a device that enhances or adds functionality to a physiological system. The term "vascular implant" may include, for example and without limitation, a stent, stent-graft, filter, valve, balloon, embolization coil, and the like.

In the present disclosure, the term "proximal" in relation to an implantable device refers to a direction that is generally closest to the heart during a medical procedure, while the term "distal" refers to a direction that is furthest from the heart during a medical procedure.

Figure 1:
FIG. 1 is a schematic illustration of a closure element in an unbiased configuration.

FIG. 1 illustrates a closure element 10 of a closure mechanism in accordance with an embodiment. The closure element in this embodiment is a wire of resiliently deformable material that, when unbiased, has a substantially flat configuration. In this example, the wire is of a shape memory material such as Nitinol. Other shape memory materials are also possible. The wire need not be of shape memory material. In modifications, other materials, such as a spring metal (for example, spring steel) could be used.

The nitinol wire has a fixation point 12 formed at each end thereof. In this embodiment, the fixation points 12 are looped or apertured ends of the closure element 10. Other arrangements may be envisaged by the skilled person.

Figure 2:
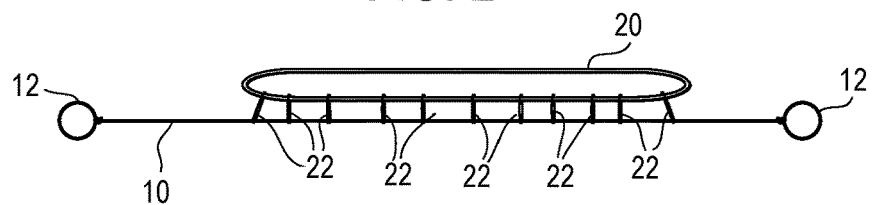
FIG. 2 is an end view of a closure element in an unbiased configuration, attached to a closed tubular portion of a vascular implant.

FIG. 2 illustrates the closure element 10 attached to a tubular portion of a vascular implant, for example, a tube of graft material 20. The graft material may include a flexible material, such as polytetrafluoroethylene (PTFE) or expanded PTFE (ePTFE), polyethylene terephthalate (PET), a polyester material, or other stent graft materials known in the art.

The closure element 10 is attached around approximately half the circumference of the tube of graft material 20 at a plurality of attachment points, which in the illustrated embodiment are provided by a plurality of closure element sutures 22. In this embodiment, the closure element 10 is attached around only half the circumference of the tube of graft material 20. As can be seen in FIG. 2, when the closure element is in its unbiased substantially flat configuration, the tube of graft material is flattened and effectively closed.

Figure 3:
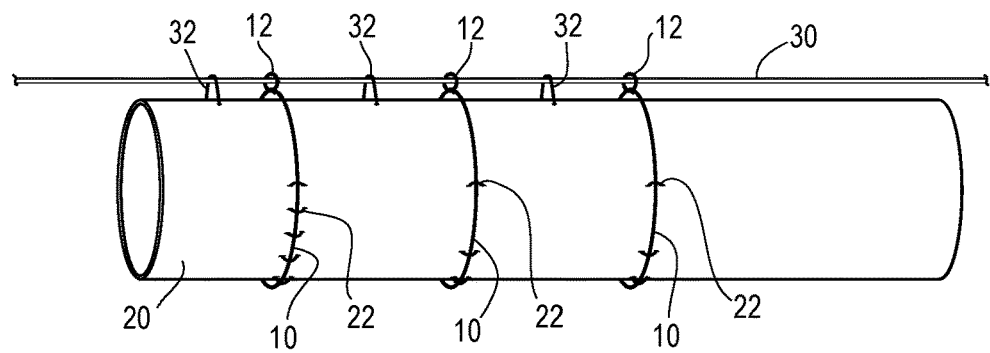
FIG. 3 is a perspective view of a closure element in a biased configuration, attached to an open tubular portion of a vascular implant.
Figure 4:
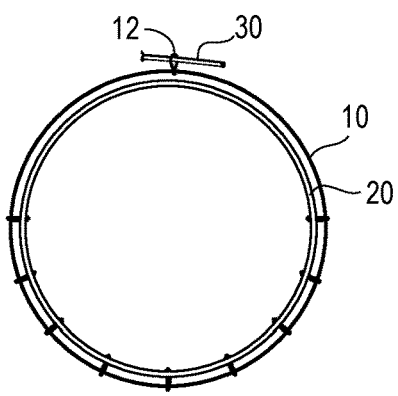
FIG. 4 is a an end view of a closure element in a biased configuration, attached to an open tubular portion of a vascular implant.

FIGS. 3 and 4 illustrate the closure element 10 held in a biased configuration by means of a release element 30 engaged with the closure element. In this case, the release element 30 is a release wire threaded through the apertured ends 12 of the closure element 10, which have been brought together causing the closure element 10 to take on a substantially annular profile. A single release wire 30 can thus hold together the apertured ends 12 of a single closure element 10. As illustrated in FIG. 3, in this embodiment where a plurality of closure elements 10 are provided, a single release wire 30 can hold several closure elements 10 in their biased, annular, configurations. Of course, the skilled person will appreciate that in some circumstances a plurality of release elements 30 may be preferred.

The tubular portion of the vascular implant, such as graft material 20, is further attached to the release wire 30 by means of release wire attachment points, in this embodiment provided by release wire attachment sutures 32 (not shown in FIG. 4, for clarity). FIG. 3 illustrates a release wire attachment suture 32 provided close to the location of each closure element 10, however, the number and position of these can be varied, as will be appreciated by the skilled person.

In use, the above-described closure mechanism provides control and choice to the user regarding closure of a tubular portion 20 of a vascular implant where this is desirable. In order to close the tubular portion, the user simply needs to withdraw or otherwise disengage the release wire 30 or other release element from the closure element 10 fixation points 12. This removes the bias from the closure element 10 causing it to take on its unbiased substantially flat profile, which at the same time, causes the tubular portion 20 of the vascular implant to flatten and close. The closure is effected substantially immediately.

In an embodiment, the above-described closure mechanism could be used in conjunction with a vascular implant. For example, it could be used to close a valve element for use with an implant such as a candy plug.

A false lumen caused by a type B aortic dissection may be treated by closing the upstream end of the false lumen for example with a stent graft.

However, in some instances, the false lumen can still receive backflow from downstream tears in the false lumen wall.

A conventional way to treat this is to use an occlusion device such as a candy plug, in particular a candy plug including a valve element. The candy plug technique is described in detail in Kölbel et al. (2013) Distal False Lumen Occlusion in an Aortic Dissection with a Homemade Extra-Large Vascular Plug: The Candy-Plug Technique *J. Endovasc. Ther.* 20, 484-9, the content of which is incorporated herein by reference. In an embodiment, the valve element is formed by a closure mechanism as described above and illustrated in FIGS. 1 to 4.

Figure 5:
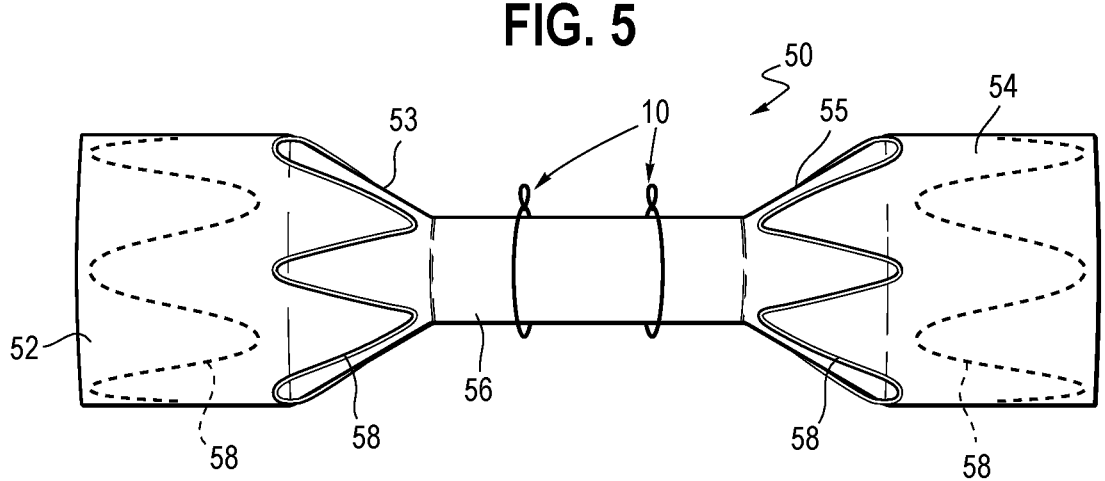
FIG. 5 is a schematic representation of a candy plug.

FIG. 5 illustrates an embodiment of a candy plug 50.

As can be seen in FIG. 5, the candy plug 50 includes an elongate support member 20 in the form of a stent graft. The support member 20 includes a proximal anchoring section 52, a distal anchoring section 54, and an intermediate section 56.

As shown in FIG. 5, the intermediate section 56 has a smaller diameter than both the proximal anchoring section 52 and the distal anchoring section 54. The diameters of the proximal anchoring section 52 and distal anchoring section 54 are approximately the same in the device shown in FIG. 5. In an example, the diameters of the proximal anchoring section 52 and the distal anchoring section 54 may be in the region of 30-46 mm, for example 10-46 mm. The intermediate section 56 may have a diameter greater than 9 mm, for example, in the region of 10-14 mm (in an embodiment the diameter is approximately 14 mm). In practice, when in its biased annular configuration, the intermediate section will be held open just wide enough that the tip of the delivery system can be retrieved therethrough. The smaller diameter of the intermediate section 56 can be caused by provision of at least one closure mechanism as described above.

As can be seen in FIG. 5, the support member 20 also includes a proximal tapering section 53 and a distal tapering section 55. The proximal tapering section 53 connects the proximal anchoring section 52 to the intermediate section 56, and the distal tapering section 55 connects the intermediate section 56 to the distal anchoring section 54.

The proximal tapering section 53 has in the deployed configuration a diameter which tapers from the proximal anchoring section 52 to the intermediate section 56. The distal tapering section 55 has in the deployed configuration a diameter which tapers from the distal anchoring section 54 to the intermediate section 56.

The elongate support member 20 includes an internal wall forming an internal lumen which is continuous through the proximal anchoring section 52, the proximal tapering section 53, the intermediate section 56, the distal tapering section 55, and the distal anchoring section 54. The intermediate section 56 is between and in fluid communication with the proximal anchoring section 52 and the distal anchoring section 54.

The support member 20 is provided by a graft material tube with, in the device of FIG. 5, four stents 58, which in this embodiment are self-expanding stents. A stent 58 is provided on each of the proximal anchoring section 52, the proximal tapering section 53, the intermediate section 56, the distal tapering section 55, and the distal anchoring section 54. The stents 58 on the proximal and distal anchoring sections 52, 54 are, for the support member 20 of FIG. 5, internal, whereas the stents 58 on the tapering sections 53, 55 are external. The skilled person will of course appreciate that other arrangements are also possible.

The intermediate section 56 of the support member 20 includes, in this embodiment, two closure mechanisms, for example of the type illustrated in FIGS. 1 to 4 above. The skilled person will, of course, appreciate that a different number of closure mechanisms may be provided depending on the circumstances. These both assist in deployment of the candy plug in vivo, and enable controlled closure of the intermediate section 56 to prevent backflow into the false lumen by occlusion of the lumen, as described below.

The candy plug 50 is delivered in a compressed configuration by means of a delivery device as known in the art (an example of which is described in more detail below with reference to FIGS. 16 to 18). Generally, a wire guide is advanced to the treatment site, and a delivery device is then advanced over the wire guide. The delivery device generally comprises an elongate carrier element or introducer cannula with a distal tip, and an outer sheath. The candy plug 50 is carried in a compressed configuration between the inner cannula and outer sheath with the inner cannula passing through the lumen of the support member 20. Further, a release element 30 (not shown in FIG. 5) is engaged with the apertured ends 12 of the closure element 10. Typically, a pusher member is included proximally of the candy plug 50 to help advance it to the desired location in a conventional manner.

Once the candy plug 50 has been delivered to the desired location, for example, within a false lumen caused by a type B aortic dissection, the outer sheath of the deployment device is retracted and the candy plug 50 is allowed to expand from the delivery device into a deployed configuration in which it seals against the walls of the false lumen. The self-expanding stents 58 are able to expand. Furthermore, the closure elements 10, being held in their biased configuration by the release wire 30, expand into their substantially annular profile, causing the lumen of the intermediate section 56 to open.

The delivery device can then be retracted. The intermediate section 56 is held open by the closure elements 10 in their substantially annular profiles, to allow the inner cannula, tip and wire guide to be retracted through the distal end of the candy plug 50 without dislodging the implant.

Once the candy plug 50 has been correctly located at the treatment site, and the delivery device has been retracted, the clinician simply needs to withdraw the release wire 30 so that it disengages from the apertured ends 12 of the closure elements 10. The closure elements 10 will then take on their substantially flat profile, closing the intermediate section 56 as they do so, as illustrated in FIG. 2.

Use of this closure mechanism with a candy plug provides several advantages. A problem with some existing candy plug assemblies is that the valve is difficult to compress radially for delivery through an introducer assembly. The disclosed closure mechanism is easily compressible, taking up little additional space on the delivery device. It avoids the need to rely on thrombosis for occlusion, which can take several months and is variable. With the present arrangement occlusion occurs substantially instantaneously. Moreover, the clinician is able to control when occlusion occurs, and can ensure the intermediate section 56 remains open to facilitate withdrawal of the delivery device prior to removal of the release wire 30 and closure of the valve.

Figure 6:
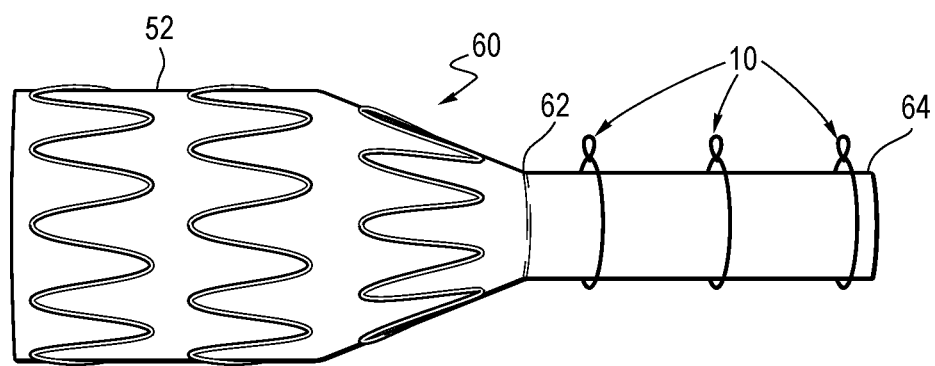
FIG. 6 is a schematic representation of an occlusion device.

FIG. 6 illustrates another embodiment of occlusion device 60 in the form of an implantable medical device having an elongate flexible tubular valve member with which the above-described closure mechanism may be used. Such an occlusion device is disclosed in EP 3 421 011, the content of which is incorporated herein by reference, and may also be useful in treating a false lumen caused by a type B aortic dissection.

The device 60 illustrated in FIG. 6 includes an elongate flexible tubular valve member 20. The elongate flexible tubular valve member 20 has an open proximal end 62 in a deployed condition of the device and a closable distal end 64.

The elongate flexible tubular valve member 20 is provided, in the embodiment shown in FIG. 6, with three closure elements 10 of a closure mechanism as described above. One of the closure elements is provided at the distal end 64 of the elongate flexible tubular valve member 20. The elongate flexible tubular valve member 20 is easily radially compressible or foldable for delivery on a delivery device. The device 60 is mounted on a delivery device similarly to the candy plug 50 of FIG. 5, with a release wire 30 (not shown) engaging the apertured ends 12 of the closure elements 10.

The embodiment of FIG. 6 is delivered to a treatment site, and is allowed to expand in vivo in a manner similar to the candy plug 50 of FIG. 5. Once the device 60 has been correctly located at the treatment site, the delivery device is retracted through the lumen of the elongate flexible tubular valve member 20 held open by the closure elements 10 biased into their substantially annular profile. The clinician then withdraws the release wire 30 so that it disengages from the apertured ends 12 of the closure elements 10. The closure elements 10 take on their substantially flat profile, closing the elongate flexible tubular valve member 20.

In an embodiment, the closure mechanism may be used with other types of vascular implant, for example, with a bidirectional branch graft, such as that described in US 2019/0021887 and EP 3 470 017, the contents of which are incorporated herein by reference.

Where damage has occurred to an internal vessel of the human or animal body such as a blood vessel either by disease or by trauma it is possible to introduce to the blood vessel a stent graft by endoluminal techniques, which will restore patency of the blood vessel across the damaged region. Often such damaged regions include side branch vessels. To ensure the blood flow can go into the side branch vessel, side branch stent grafts are used.

Endovascular aortic aneurysm repair is practised by a wide range of physicians across varying specialties. An aortic aneurysm is an enlargement of the aorta of a patient caused by weakening in the wall of the aorta. If an aortic aneurysm is untreated, it may rupture and cause serious health complications.

The surgical procedure for endovascular aortic aneurysm repair involves the placement of a stent graft within the aorta of a patient to seal off the aneurysm from blood flow to prevent the aneurysm from expanding. Physicians often use the procedure to treat abdominal aortic aneurysms (AAA), thoracic aortic aneurysms (TAA), thoraco-abdominal aortic aneurysms (TAAA), and aneurysms in other parts of a patient's anatomy.

The aorta has many branches to other vessels or arteries, such as the renal arteries, the superior mesenteric artery (SMA), the inferior mesenteric artery, and the left and right internal iliac arteries. Branch vessels are also connected to the head, arms, spinal cord, intestines and/or kidneys. Endovascular repair of aneurysms occurring at or near branch vessels requires that blood flow to the branch vessel is maintained and access to the branch vessel for cannulation is available.

Stent grafts may include internal branches to cannulate branch vessels and to maintain blood flow to the branch vessels. However, these internal branches often only include a small opening or access in one direction within the stent graft for physicians to cannulate the branch vessel. Frequently it is unknown or not clear from which direction the branch vessel is best cannulated. These factors increase the difficulty of cannulation, which can lead to complications during the surgical procedure for endovascular aortic aneurysm repair.

US 2019/0021887 and EP 3 470 017 describe a method of making an internal bidirectional branch in which an internal bidirectional coupling insert is located internally within a main lumen of an endoluminal prosthesis.

With the construction and positioning of the internal bidirectional coupling insert, during cannulation, a cannula or tube may be inserted through an opening of the internal bidirectional coupling insert and then exit the internal bidirectional coupling insert either through a distal end thereof towards the distal end of the endoluminal prosthesis or through a proximal end of the internal bidirectional coupling insert towards the proximal end of the endoluminal prosthesis. Alternatively, the cannula or tube may be inserted through the internal bidirectional coupling insert either through the distal end of the internal bidirectional coupling insert and out of the opening or through the proximal end of the internal bidirectional coupling insert and out of the opening.

An embodiment of an internal bidirectional coupling insert that incorporates a closure mechanism, such as that described with reference to FIGS. 1 to 4, is illustrated in FIGS. 7 to 10.

FIGS. 7 and 8 illustrate a tubular branch coupling insert in the form of an internal bidirectional coupling insert 70 in accordance with an embodiment. This provides a coupling insert lumen having a coupling insert circumference. In the illustrated embodiment, the internal bidirectional coupling insert includes a closure mechanism as illustrated in FIGS. 1 to 4. However, the skilled person will appreciate that other closure mechanisms are possible. At least one closure element 10 extends around the coupling insert circumference and is attached to the coupling insert 70. In this embodiment, the apertured ends 12 of the closure elements are longitudinally aligned along the internal bidirectional coupling insert 70.

The bidirectional coupling insert 70 is preferably formed from a tube of graft material. An opening 72 is provided approximately half-way along, effectively separating the coupling insert 70 into two branch portions, one extending proximally of the opening 72, the other extending distally. The opening 72 is, in this embodiment, located circumferentially approximately opposite the opening 72. A plurality of closure elements 10 are disposed along a length of the coupling insert 70, preferably in a spaced relationship. In this embodiment, three closure elements 10 are provided proximally of the opening 72, and three are provided distally of the opening 72, although in other embodiments there may be different numbers of closure elements 10 provided proximally and distally. In practice there will be at least two provided, and one of these will be provided at the proximal end of the insert 70 and another at the distal end of the insert. In many embodiments a plurality of closure elements 10 will be provided proximally of the opening 72, and a plurality of closure elements 10 will be provided distally of the opening 72.

A release wire 30 engages the apertured ends 12 of the closure elements 10 in order to bias them into their annular profile. The bidirectional coupling insert 70 is provided within the main lumen of an endoluminal prosthesis (not shown in FIGS. 7 and 8), the opening 72 of the bidirectional coupling insert 70 being aligned with a fenestration in a side wall of the endoluminal prosthesis, which in use, is to be aligned with a branch vessel.

Figure 9:
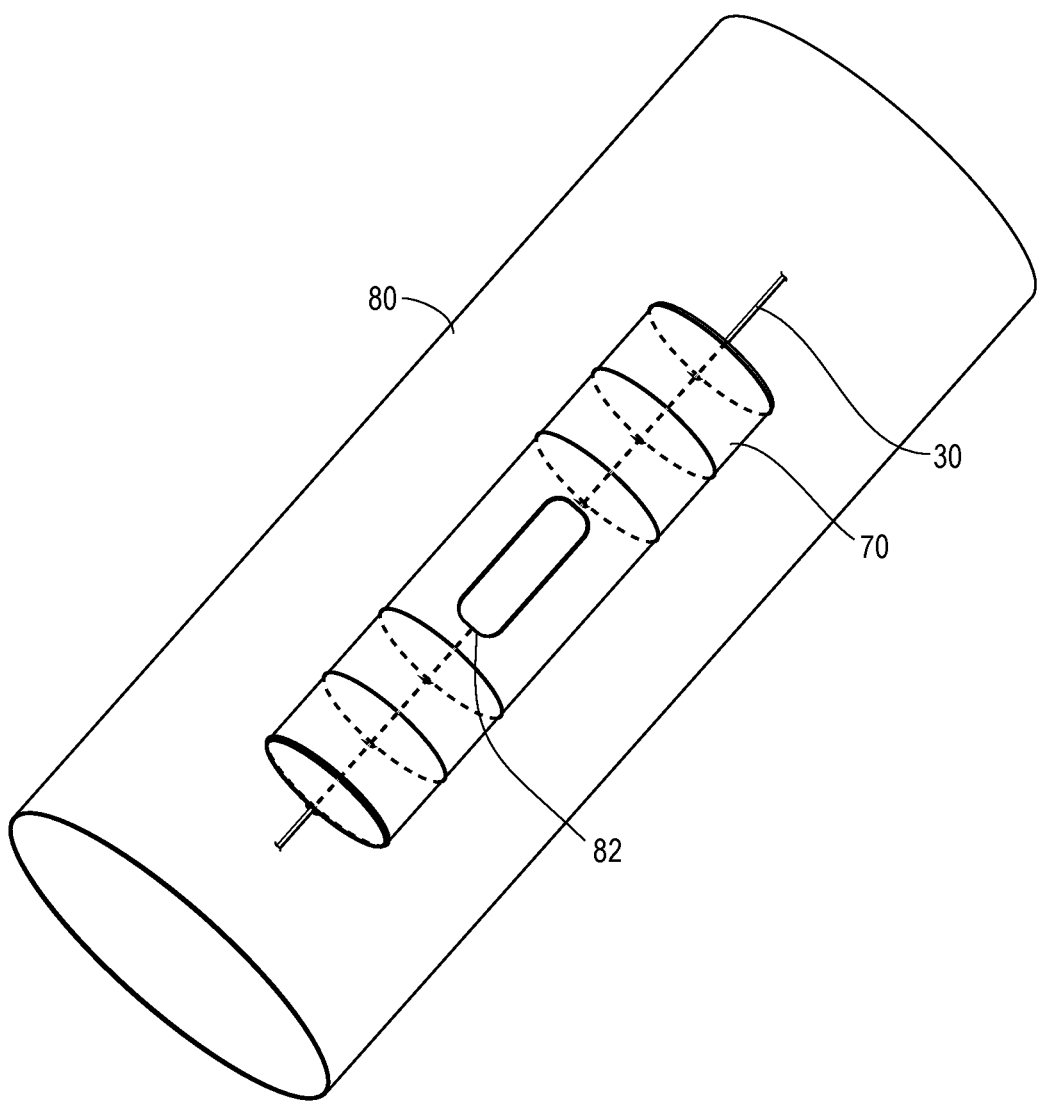
FIG. 9 illustrates the internal bidirectional coupling insert of FIGS. 7 and 8 positioned within a main lumen of an endoluminal prosthesis.

FIG. 9 schematically illustrates a tubular main body portion in the form of an endoluminal prosthesis 80 providing a main graft lumen and having a fenestration 82 in a side wall thereof. The endoluminal prosthesis 80 may be suitable for positioning within a patient's aorta, in the region of a branch vessel.

A bidirectional coupling insert 70 is disposed within the main lumen of the endoluminal prosthesis 80, and is attached thereto at least at the location of the side wall opening 72 of the bidirectional coupling insert, which is aligned with the side wall fenestration 82 of the endoluminal prosthesis. For example, the bidirectional coupling insert 70 may be stitched to the endoluminal prosthesis 80 around the peripheries of their respective opening 72 and fenestration 82.

The graft assembly is deployed in a vessel of a patient with the closure element 10 in the biased configuration so as to the hold the lumen of the coupling insert 70 in an open configuration. It can be seen that both ends of the bidirectional coupling insert 70 are held open by way of the closure elements 10 being biased into their annular profiles by the release wire 30. The deployment method includes the step of disposing a branch graft 84 in the branch coupling insert 70 while the lumen of the coupling insert 70 is in the open configuration. It can be seen from FIG. 9 that the surgeon thus has a degree of choice regarding in which direction to insert the branch graft 84, and can decide based on the individual patient's anatomy, the clinical picture for the particular treatment being undertaken, or even in some instances, personal preference.

Figure 10:
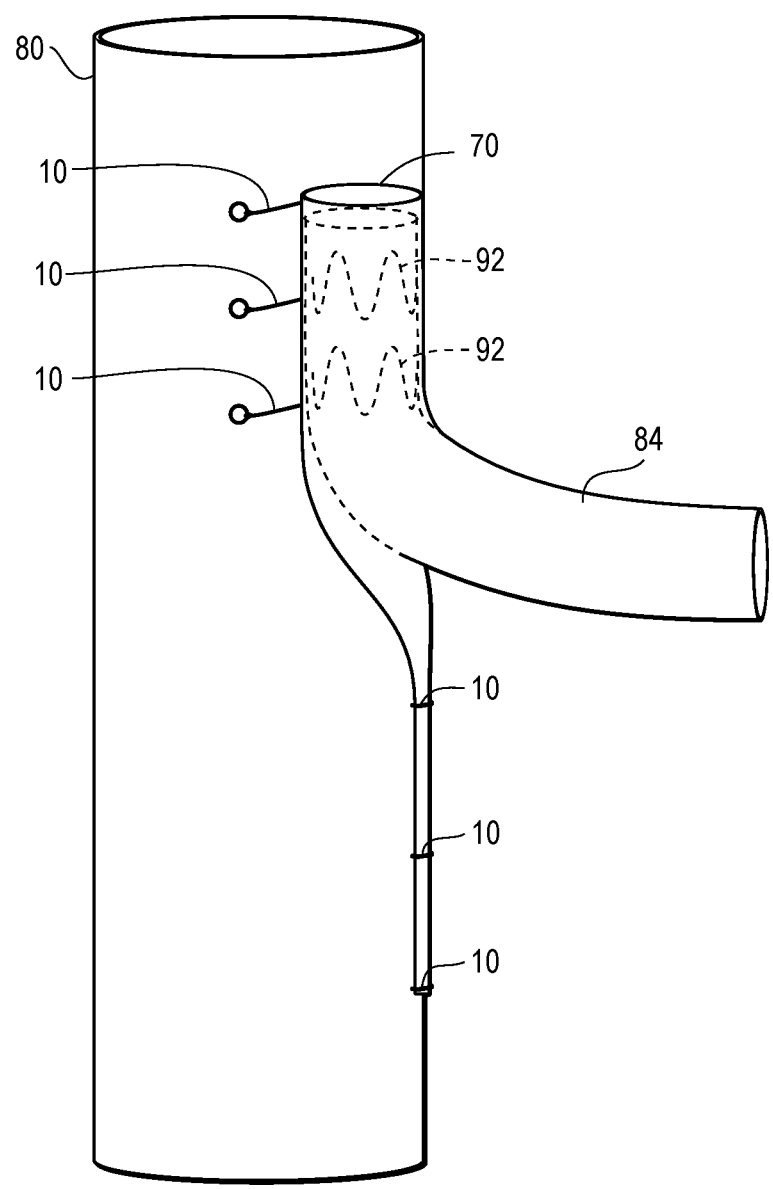
FIG. 10 illustrates a graft assembly including an internal bidirectional coupling insert positioned within a main lumen of an endoluminal prosthesis, and a branch graft.

In FIG. 10, a branch graft 84 is shown disposed through the fenestration 82 and opening 72 and into, in this case, the proximal end of the bidirectional coupling insert 70 so as to be in fluid communication with the main lumen of the endoluminal prosthesis 80. FIG. 10 illustrates the arrangement after insertion of the branch graft 84, and then subsequent removal of the release wire 30 from the closure elements 10. Although FIG. 10 shows an arrangement where the branch graft 84 is inserted into the proximal end of the bidirectional coupling insert 70, this description applies equally to a branch graft 84 is inserted into the distal end of the bidirectional coupling insert 70.

The method of deploying the graft assembly includes the step of disposing a branch graft 84 in the first branch portion (for example, the proximal end of the coupling insert 70, as illustrated in FIG. 10) and releasing the bias on at least the second branch portion (for example, the distal end of the coupling insert 70) thereby to close the second branch portion.

In the illustrated embodiment, the deployment method includes the step of disposing a branch graft 84 in the first branch portion and releasing the bias on both the first and second branch portions, whereby a scaffold 92 provided on the branch graft 84 maintains the first branch portion in the open configuration. The branch graft 84 includes at least one scaffold, for example a stent 92 (illustrated in FIG. 10) for expanding or maintaining the branch graft 84 in an open tubular configuration when disposed in the bidirectional coupling insert 70.

The bias in the closure element 10 is then removed (in this embodiment by removing the release wire 30) to allow the closure element 10 to return to its unbiased configuration thereby to cause the closure element to close the lumen of the coupling insert 70. With the arrangement shown in FIG. 10, after removal of the release wire 30, the closure elements 10 tend toward their flat profiles in order to close the bidirectional coupling insert 70.

As can be seen, the distal end is closed, as the closure elements 10 flatten, and pull it closed. However, the proximal end remains open despite removal of the release wire 30 due to the expanded stents 92 holding the branch graft 84 and thus also the proximal end of the bidirectional coupling insert 70 open. By providing at least one closure element 10 on each end of the bidirectional coupling insert, one or both of the ends may be selectively closed.

The force exerted by the stents 92 overcomes the tendency of the closure element 10 to flatten, and so fluid communication between the branch graft 84 and the main lumen of the endoluminal prosthesis 80 can be maintained. The stents 92 may self-expanding. However, in some embodiments they may be balloon expandable. For example, a pressure of up to 15 atm may be used to expand a stent having a diameter of 8 mm.

The present embodiments therefore enable cannulation through at least two directions within the bidirectional coupling insert 70. Specifically, cannulation may occur through either the proximal end or the distal end of the bidirectional coupling insert 70. The multiple exits of the bidirectional coupling insert 70 allow for the insertion of multiple cannulas or tubes with decreased interference within the bidirectional coupling insert 70 and the ability to access the branched vessel from different directions within the endoluminal prosthesis 80.

Furthermore, by collapsing and thereby sealing the portion of the bidirectional coupling insert 70 that is not used to accommodate the branch graft 84, endoleakage resulting from an incomplete seal between the branch graft 84 and the main graft 80 is prevented.

In other embodiments the method of deployment may include closing the first branch portion so as to close fluid access to the first branch portion, and leaving the second branch portion open. The skilled person may readily envisage such modifications depending on the need and/or use.

Figure 11:
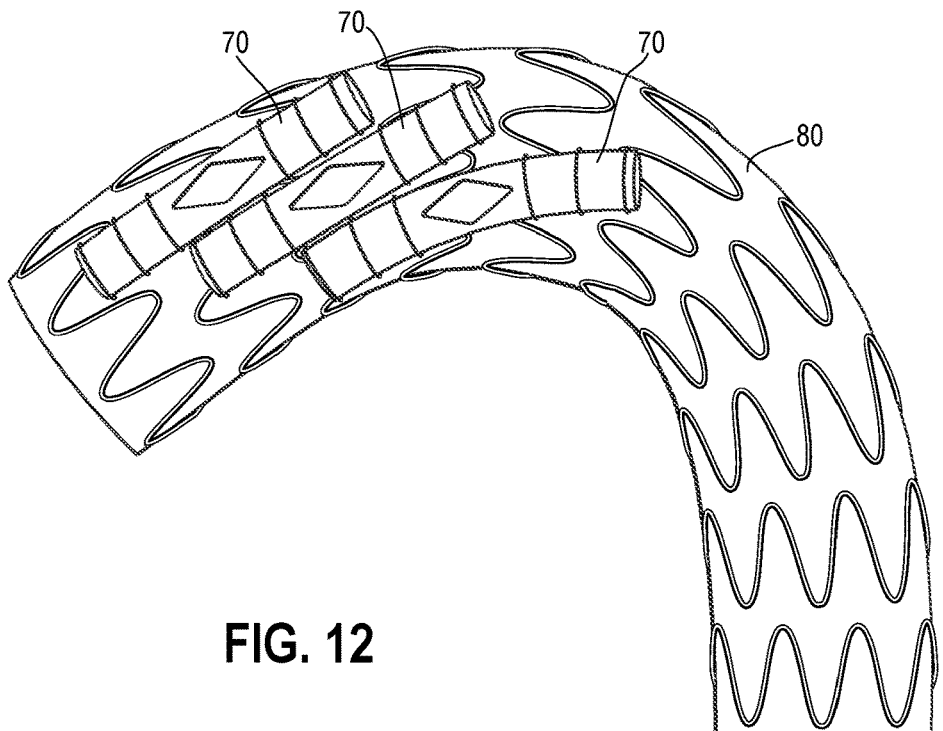
FIG. 11 is a schematic illustration of a graft assembly including a plurality of internal bidirectional coupling inserts for use in the aortic arch.

The skilled person will appreciate that the above-described graft assembly for use in the aorta in a region having a side vessel is merely exemplary to illustrate the principles of this disclosure. Modifications can readily be made in order to render the system useful for other areas of anatomy. For example, FIG. 11 illustrates an arched endoluminal prosthesis 80 provided with three bidirectional coupling inserts 70. Such an assembly could be used in the aortic arch, and the fenestrations 82 can be aligned with the brachiocephalic artery, the left common carotid artery and the left subclavian artery.

Figure 12:
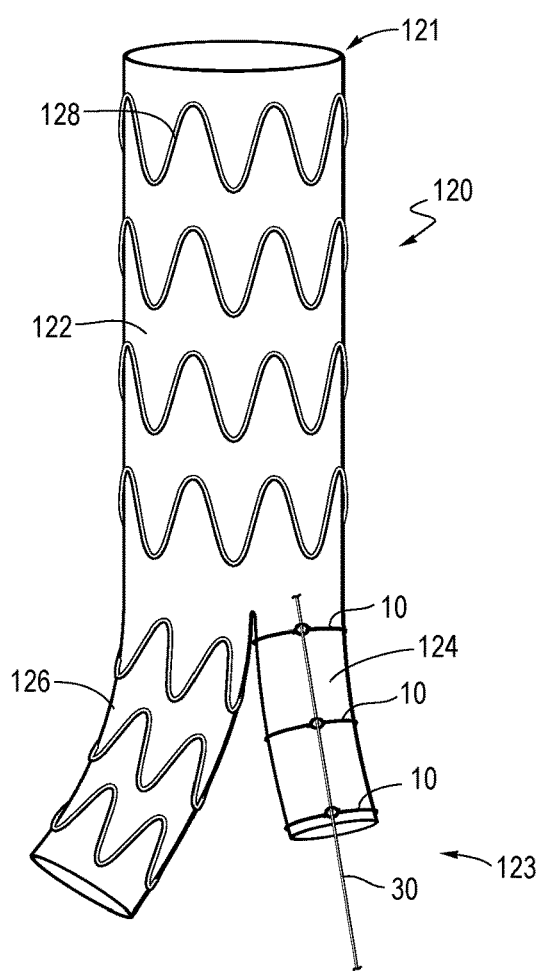
FIG. 12 illustrates an example of a bifurcated endoluminal prosthesis.

FIG. 12 illustrates another example of vascular implant that can advantageously be selectively closed. In this embodiment, the vascular implant is a bifurcated endoluminal prosthesis, in this case a bifurcated stent graft 120. Bifurcated medical devices may be implanted for the repair of an aneurysm at or in the vicinity of the aortic bifurcation. Typically, and as illustrated in FIG. 12, a bifurcated stent graft 120 comprises a main body portion 122 and first and second tubular leg portions 124, 126 joining the main body portion 122 in a bifurcation. In the device according to embodiments of the present invention, the main body portion 122 and one of the legs 126 are stented. It can be seen, however, that the other leg 124 is unstented More specifically, the main body 122 of the bifurcated stent graft 120 includes a proximal end 121 and a distal end 123. The two legs 124, 126 extend distally from the main body 122. The legs 124, 126 may be identical or may differ. For example, the branches may have the same or different lengths, the same or different widths, may be symmetrical or asymmetrical, or may comprise the same or different materials. In the example of FIG. 12, the legs are of equal width, but the stented leg 126 is longer than the unstented leg 124.

As shown, the proximal end 121 of the bifurcated stent graft 120 may include an anchor, such as a stent 128. Suitable anchors also include any means for attaching a medical device to a body vessel wall, for example suturing, stapling, searing, bonding, gluing, bioadhesives, and the like. The anchor 128 may be attached or adhered to the main graft by any means, including but not limited to welding, stitching, bonding, and adhesives.

A closure mechanism is provided on the unstented leg 124. Preferably, the closure mechanism is as described above and as illustrated in FIGS. 1 to 4, which allows the clinician to control when closure occurs. In the embodiment illustrated in FIG. 12, a plurality of (for example, three) closure elements 10 are disposed along a length of the unstented leg 124, in a spaced relationship. As with the embodiments described above, a release element 30 (for example, a release wire) is provided to hold the closure elements 10 in their biased configuration and therefore to hold the unstented leg 124 in an open configuration.

Figure 13:
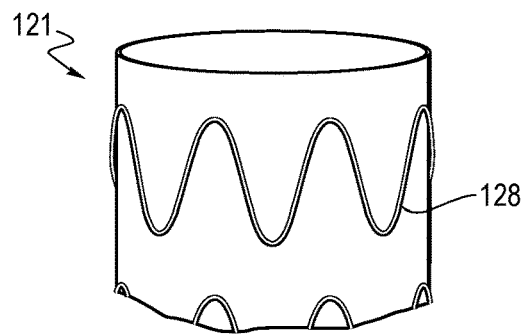
FIGS. 13 to 15 illustrate possible anchor arrangements for the proximal end of a prosthesis such as that illustrated in FIG. 12.
Figure 14:
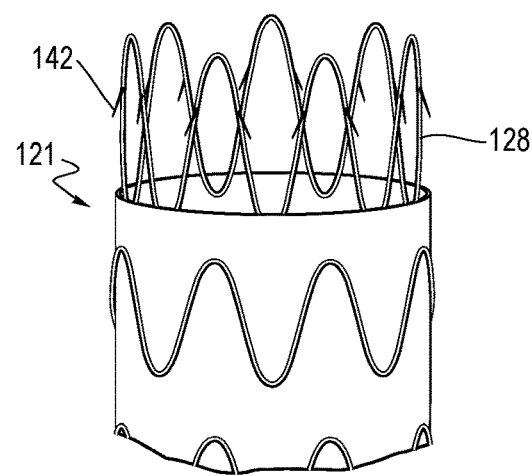
Figure 15:
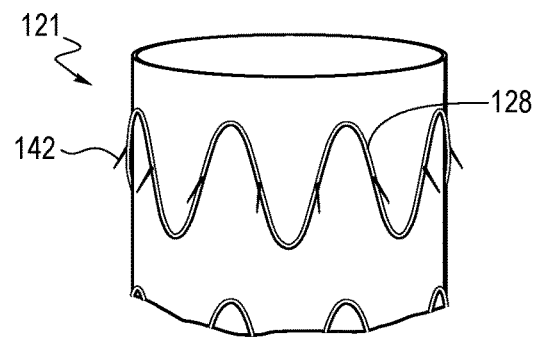

FIGS. 13 to 15 illustrate the proximal ends 121 of three embodiments of bifurcated endoluminal prosthesis 120 and three possibilities for the anchor stent 128, depending on the preference of the user and/or the clinical situation. FIG. 13 shows a sealing stent 128. This uses radial force and is useful where it would be undesirable to have barbs engaging the vessel wall. Providing the anchor stent on the inside of the stent graft 120 provides good vessel wall apposition. FIG. 14 illustrates a proximally extending bare stent 128 with barbs 142. This arrangement provides high wall apposition and includes two elements that create fixation and sealing. FIG. 15 illustrates a sealing stent 128 with barbs 142. This design can be useful where there are anatomical limitations (such as angulation) where lack of space means the design shown in FIG. 14 is inappropriate.

In use, the bifurcated stent graft 120 is compressed onto a delivery device for delivery to the aorta at the aortic bifurcation. Once at the correct location, the surgeon has the option of whether the unstented leg 124 should remain open or be closed. For example, in some patients flow into one of the common iliac arteries might be compromised by calcifications. In such a case the decision might be made to surgically restore flow to the leg at a lower level, and then to close the unstented leg 124 of the bifurcated stent graft 120.

In order to close the unstented leg 124, the user simply needs to withdraw or otherwise disengage the release wire 30 or other release element from the closure element 10 fixation points 12 as described above. This removes the bias from the closure element 10 causing it to take on its unbiased substantially flat profile, which at the same time, causes the unstented leg 124 to flatten and close. The closure is effected substantially immediately. In cases where only one of the legs needs to be maintained in an open configuration, the closure mechanism can be used to provide effective closure of the other leg substantially immediately, and without the need to rely upon thrombosis.

The bifurcated endoluminal prosthesis 120 has been described as including the closure mechanism illustrated in FIGS. 1 to 4, though the skilled person will appreciate that other ways of achieving selective closure are possible. The preferred closure mechanism provides control and choice to the user regarding closure of a leg of a bifurcated endoluminal prosthesis 120 where this is desirable. In order to close the closable leg 124, the user simply needs to withdraw or otherwise disengage the release wire 30 from the closure element fixation points 12. This removes the bias from the closure elements 10 causing it to take on its unbiased substantially flat profile, which at the same time, causes the closable leg 124 of the prosthesis 120 to flatten and close. The closure is effected substantially immediately.

With this arrangement and the possibility of selectively closing a leg portion of a bifurcated endoluminal prosthesis, a single device can have three applications. It can be used as a standard abdominal aortic aneurysm device, in which case both legs are kept open. For this, a scaffold, for example, a stent ring, would need to be placed into the unstented leg 124 prior to removal of the release wire 30 in order to hold the unstented leg 124 open. To achieve this, prior to pulling the release wire 30 for closing the unstented leg 124, a guide wire is placed into the unstented leg 124 using known techniques, and the stent ring or other scaffold is deployed into the unstented leg 124 and expanded to keep the unstented leg 124 open after closure of the closure mechanism. If one leg is closed the device can be used as an aorto-uni-iliac device or a converter. This replaces the need for separate converters or aorto-uni-iliac devices.

Although the bifurcated stent graft 120 has been described for use at the aortic bifurcation, the skilled person will appreciate that similar arrangements could be used elsewhere where bifurcations occur in the vascular system.

Figure 16:
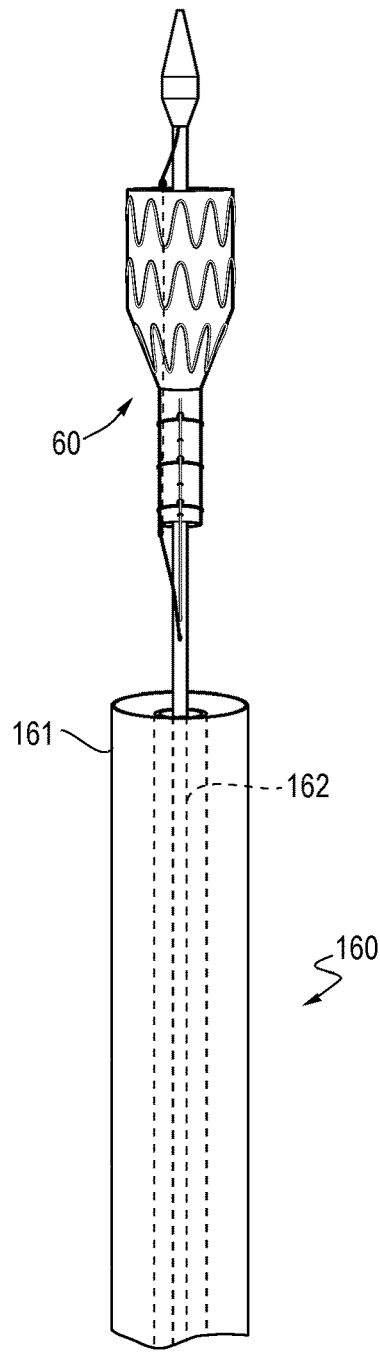
FIGS. 16 to 18 illustrate an introducer assembly for deploying a vascular implant including a closure mechanism as described herein.
Figure 17:
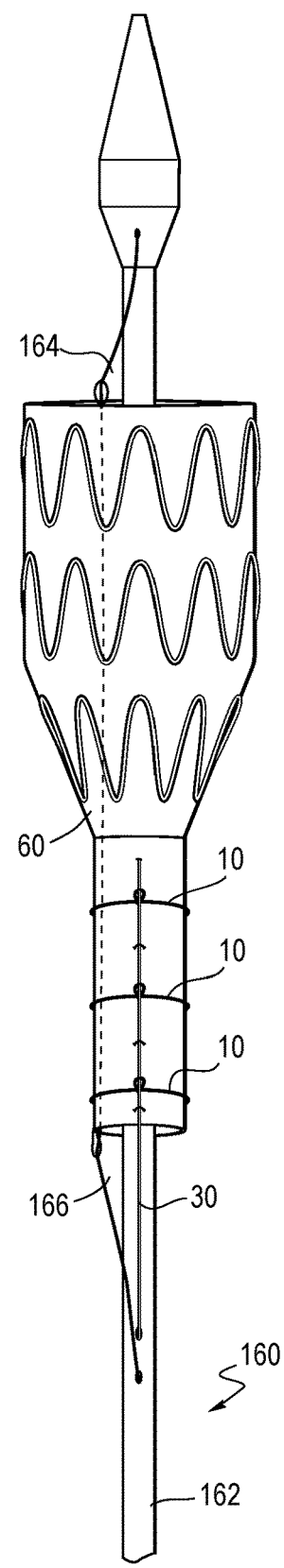
Figure 18:
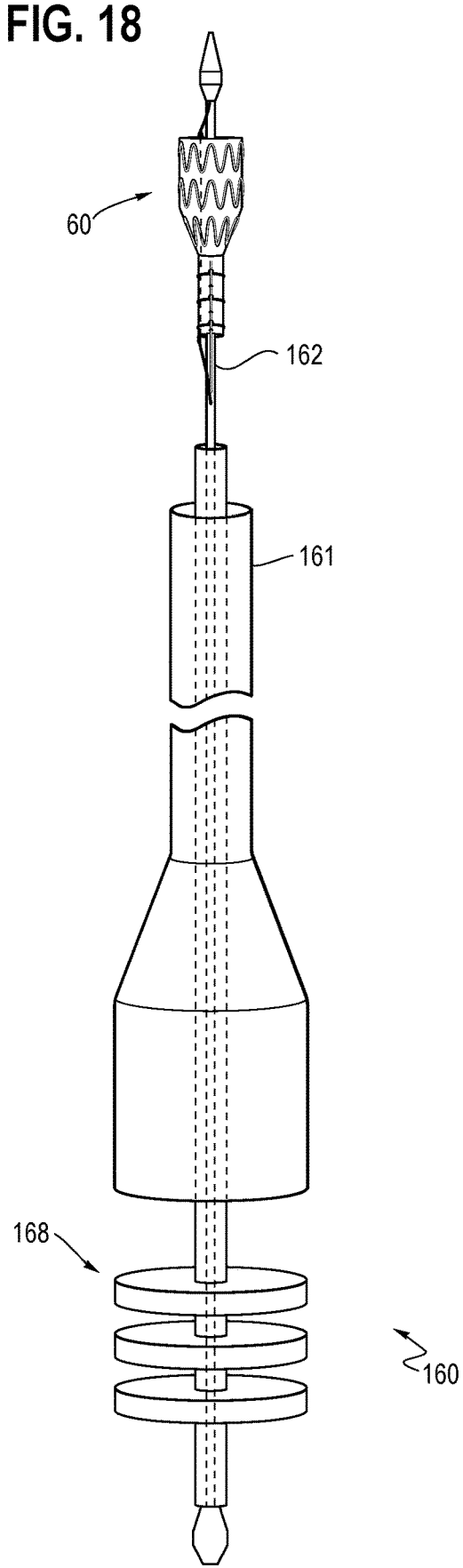

FIGS. 16 to 18 illustrate an introducer assembly 160 for deploying a vascular implant including a closure mechanism as described above and illustrated with reference to FIGS. 1 to 4. Whilst an occlusion device 60 such as that illustrated in FIG. 6 is shown, the skilled person would readily be able to adapt the introducer assembly to carry and deploy embodiments of graft assembly, prosthesis or occlusion device such as those described above. The introducer assembly 160 includes an elongate carrier element 162 configured to carry the occlusion device 60. At least one release element or release wire 30 is connected to the closure elements 10 and configured to bias the at least one closure element 30 in the biased configuration on deployment of the occlusion device 60. The release element or wire 30 maintains the lumen in an open configuration until it is withdrawn. In this example, the release wire 30 is threaded through the aperture ends 12 of the closure elements 10 as described above.

In the illustrated embodiment, the introducer assembly includes three release wires. Proximal and distal release wires 164, 166 hold the device to the introducer 160 and are attached to release knobs 168 at the manipulation end of the introducer 160 in a known manner. The release wire 30 is also attached to a release knob 168.

For delivery, the device 60 is compressed onto the elongate carrier element 162, and typically, covered by a sheath 161. After delivery of the device to the desired location of the patient's anatomy using the introducer assembly 160, the sheath 161 is withdrawn and the device 60 allowed to expand (as shown in FIGS. 16 to 18). The expansion may occur automatically by use of self-expanding stents. In other embodiments the device may be balloon-expandable. The release knobs are used to withdraw the release wires 164, 166 after which the introducer assembly 160 can be retracted through the expanded device.

Once the introducer assembly 160 has been retracted, sufficiently that it is clear of the implanted device, the release wire 30 can be withdrawn or otherwise disengaged from the closure elements 10, thereby causing these to flatten and close the lumen as described above. As will be appreciated the release wire 30 should have a length greater than that of the distance between its release knob 168 and the point at which it is engaged with the closure elements 10. For example, the release wire 30 may include a loop. The loop could be inside or outside the device. The length of the loop will be such that the release wire 30 does not disengage from the closure elements 10 before the introducer assembly has been retracted beyond the distal end of the device. The introducer assembly can then be removed from the patient.

In an embodiment where the vascular implant is a graft assembly including a tubular branch coupling insert. In this embodiment the introducer assembly may include a second elongate carrier configured to carry a branch graft 84, the second elongate carrier being configured to deploy the branch graft 84 into at least a portion of the branch coupling insert 70.

The branch coupling insert 70 may be a bidirectional member having first and second branch portions, the first and second branch portions being coupled to a main graft or endoluminal prosthesis 80 such that the coupling insert lumens of the first and second branch portions are in fluid communication with the main graft lumen Closure elements 10 may be provided on each of the branch portions, the at least one release element or wire 30 being releasably engaged with the closure elements 10.

In an embodiment where the vascular implant is a bifurcated endoluminal prosthesis 120, and the unstented leg 124 is to remain open, a second elongate carrier may be used to to carry a scaffold for deployment into the unstented leg 124 prior to disengagement of the release element 30 from the closure mechanism.

It will be appreciated by those skilled in the art that changes could be made to the embodiments described above without departing from the broad inventive concept. It is understood, therefore, that this invention is not limited to the particular embodiments disclosed, but it is intended to cover modifications within the spirit and scope of the present invention as defined by the claims.

The disclosure of the accompanying abstract is incorporated herein by reference.

The invention claimed is:

1. A graft closure system for closing a portion of a graft comprising:
   a graft having a tubular portion, a lumen and a circumference;
   a closure mechanism including at least one closure element extending around the circumference of the tubular portion and attached to the tubular portion, the at least one closure element comprising a resiliently deformable material and having a first, biased, configuration in which the closure element has a generally annular profile and a second, unbiased, configuration in which the closure element has a substantially linear profile; and
   a release element engaged with the closure element;
   wherein in the first, biased, configuration the closure element holds the tubular portion lumen in an open configuration and in the second, unbiased, configuration the closure element holds the tubular portion lumen in a closed configuration; and
   wherein the release element is configured to disengage from the closure element to move the closure element from the first, biased configuration to the second, unbiased configuration and closes the lumen.

2. The graft closure system of claim 1, wherein the at least one closure element comprises a plurality of closure elements disposed along a length of the tubular portion.

3. The graft closure system of claim 1, wherein the at least one closure element has first and second ends, each end including a release element fixation point, wherein the release element fixation points are fixed adjacent or over one another and engage the release element such that the at least one closure element is held in the first, biased, configuration.

4. The graft closure system of claim 3, wherein the release element fixation points comprise loops or apertures at the ends of the at least one closure element.

5. The graft closure system of claim 1, wherein the tubular portion is a limb of a bifurcated stent graft, a length of a tubular stent graft, and/or an internal or external branch of a branched stent graft.

6. The graft closure system of claim 5, wherein the tubular portion is a bidirectional branch disposed within a lumen of a main graft and coupled to the main graft and having first and second branch portions, wherein the at least one closure element is disposed about the circumference of at least one of the first and second branch portions in the first, biased, configuration.

7. The graft closure system of claim 6, wherein the bidirectional branch has a first open end, a second open end and a fenestration communicating with a fenestration in a side wall of the main graft.

8. The graft closure system of claim 1, wherein the release element is a retractable wire.

9. The graft closure system of claim 8, wherein the at least one closure element comprises shape memory material.

10. A branched graft comprising:
    a tubular main body providing a main graft lumen;
    a branch coupled to the main body and having a branch lumen and at least one branch circumference;
    the branch including at least one closure element extending around the branch circumference and attached to the branch, the at least one closure element comprising a resiliently deformable material and having a first, biased, configuration in which the closure element has a generally annular profile about the circumference of the branch and a second, unbiased, configuration in which the closure element has a substantially linear profile
    wherein in the first, biased, configuration the at least one closure element holds the branch lumen in an open and substantially annular configuration and in the second, unbiased, configuration the closure element holds the branch lumen in a substantially closed configuration.

11. The branched graft of claim 10, wherein the at least one closure element comprises a plurality of closure elements disposed along a length of the branch member and about the circumference of the branch.

12. The branched graft of claim 10, wherein the at least one closure element has a first end comprising a first loop or aperture, a second end comprising a second loop or aperture, and a release wire extending through the first and second loops or apertures to hold the at least one closure element in the first, biased, configuration.

13. The branched graft of claim 10, wherein the branch is disposed within the tubular main body lumen.

14. The branched graft of claim 13, wherein the branch is bidirectional and has a first branch portion extending toward a first end of the branched graft, a second branch portion extending toward a second end of the branched graft, and a lumen in fluid communication with the tubular main body lumen, wherein the at least one closure element is disposed on at least one of the first and second branch portions.

15. The branched graft of claim 14, wherein a first closure element of the at least one closure element is disposed on the first branch portion and a second closure element is disposed on the second branch portion and are configured to provide selective closure of one of or both of the first and second branch portions.

16. The branched graft of claim 10, wherein the branch is disposed external to the tubular main body lumen.

17. A graft closure system for selectively closing a lumen of a graft comprising:
a tubular graft portion having at least one lumen and a circumference,
a closure mechanism including a plurality of closure elements extending around the circumference of and along the length of the tubular graft portion and attached to the tubular graft portion, the plurality of closure elements comprising a resiliently deformable material having a first, biased, configuration in which the closure element has a generally annular profile and a second, unbiased, configuration in which the closure element has a substantially linear profile, and
a release element engaged with first and second ends of each of the plurality of closure elements in the first, biased, configuration;
wherein in the first, biased, configuration the closure elements hold the at least one lumen in an open tubular configuration and in the second, unbiased, configuration the closure element holds the at least one lumen in a closed configuration; and
wherein the release element is configured to disengage from the plurality of closure elements and move the closure elements from the first, biased configuration to the second, unbiased configuration and closes the at least one lumen.

18. The graft closure system of claim 17, wherein the plurality of closure elements each has first and second ends, each end including a release element fixation point, wherein the release element fixation points are fixed adjacent or over one another and engage the release element such that the at least one closure element is held in the first, biased, configuration.

19. The graft closure system of claim 18, wherein the release element fixation points comprise loops or apertures at the ends of the at least one closure element.

20. The graft closure system of claim 17, wherein the release element is a retractable wire.

* * * * *